(12) United States Patent
Barclay (10) Patent No.: US 7,018,623 B2
(45) Date of Patent: Mar. 28, 2006

(54) B COMPLEX VITAMIN COMPOSITIONS THAT PROTECT AGAINST CELLULAR DAMAGE CAUSED BY ULTRAVIOLET LIGHT

(76) Inventor: Barry J. Barclay, 76 Gordon Crescent, St. Albert, Alberta (CA) T8H 0V8

( * ) Notice: Subject to any disclaimer, the term of this patent is extended or adjusted under 35 U.S.C. 154(b) by 37 days.

(21) Appl. No.: 09/900,064

(22) Filed: Jul. 6, 2001

(65) Prior Publication Data

US 2002/0035087 A1 Mar. 21, 2002

(51) Int. Cl.
*A61K 7/42* (2006.01)
*A61K 7/44* (2006.01)
*A61K 7/00* (2006.01)

(52) U.S. Cl. .......................... 424/59; 424/60; 424/400; 424/401

(58) Field of Classification Search ................. 424/59, 424/60, 400, 401
See application file for complete search history.

(56) References Cited

U.S. PATENT DOCUMENTS 6,251,878 B1 * 6/2001 Strickland et al. ............ 514/54

OTHER PUBLICATIONS

Article (on-line) Jun. 10, 2000 'Company Launches Sunburn Pill' *Press Release* www.pressbox.co.uk.
Tenth International Symposium; Chemistry and Biology of Pteridines and Folates; Orange Beach Alabama; Mar. 21-26, 1993; Final Program and Abstract Book: B12—B.J. Barclay et al.; "Effect Of Chromosome Position On Amplification Of The DHFR Gene In Saccharomyces Cerevisiae" B-13—B.J. Barclay et al.; "A DHFR Mutant Of Saccharomyces Cerevisiae Is Defective In DNA Repair" B-14—T. Huang et al.; Phenotypic Suppressors Of A Dihydrofolate Reductase Mutant Of Saccharomyces Cerevisiae B-15—M.G. Nagel et al.; "Dihydrofolate Reductase Is Not The Target Of Trimethoprim In Saccharomyces Cerevisiae".

* cited by examiner

*Primary Examiner*—Shelley A. Dodson
(74) *Attorney, Agent, or Firm*—Nields & Lemack (57) ABSTRACT

The present invention relates generally to the use of vitamin B12 (cobalamin or cyanocobalamin) alone or in combination with other photoprotective agents, including specifically other vitamins such as vitamin B9 (folic acid or folate) and vitamin B3 (niacin or niacinamide), or any chemical derivative of these vitamins and their salts, as a filter to protect cells against the damaging effects of ultraviolet (UV) light. The invention is, in one aspect, a method of reducing the rate of UV damage to cells exposed to a UV light source, by treating the cells with the vitamin composition, either alone or in combination with other photoprotective agents. Other aspects of the invention are compositions comprising effective amounts of vitamin B12 alone or in combination with other photoprotective agents including vitamin B9 and vitamin B3 and a pharmaceutically-acceptable carrier, that are useful in protecting cells, particularly skin cells, against the burning, genotoxic (mutagenic and carcinogenic), immunosuppressive and photoaging effects of UV light, especially sunlight. The invention has application as a UV light filter in oral preparations including tablets and drinks, topical creams, lotions, sprays, wipes and cosmetics. The invention also has application as a medicinal treatment for dermatological conditions caused by exposure to sunlight, such as actinic keratoses, photodermatitis, photo-induced (discoid) lupus erythematosus and the photosensitizing effects of a variety of drugs used commonly in clinical practice (e.g. certain antihistamines, ACE inhibitors, and antibiotics such as tetracycline).

37 Claims, 3 Drawing Sheets

B COMPLEX VITAMIN COMPOSITIONS THAT PROTECT AGAINST CELLULAR DAMAGE CAUSED BY ULTRAVIOLET LIGHT

FIELD OF THE INVENTION

The invention relates generally to sunscreens and sunfilters, and to methods and compositions for protecting cells against the damaging effects of sunlight and artificial sources of UV light such as lamps and arc welding equipment. In particular, the invention is directed to the use of vitamin B12, alone or in combination with folate (used here to refer to all of the folic acid derivatives found commonly in nature), and niacin (specifically niacinamide) in methods and compositions for protecting cells and organisms including humans against the burning, genotoxic, immunosuppressive and photoaging effects of exposure to UV light.

BACKGROUND OF THE INVENTION

Over the past several decades, the worldwide incidence of skin cancer has been increasing at an alarming rate. The reason for the dramatic increase in skin cancers that has occurred over this period and the human suffering associated with these diseases is not entirely clear. Many experts believe that it is due, at least in part, to depletion of the earth's protective ozone layer. The widespread use of sunscreens that protect against some but not all of the sun's harmful UV radiation (UVB but not UVA) has also played a role. According to the National Cancer Institute (NCI), there will be over one million new cases of skin cancer reported in the United States in the year 2001 and approximately 7000 deaths. This nears the total of all other cancers combined. NCI also reports that if present trends continue 40–50% of fair skinned Americans now living are expected to develop at least one type of skin cancer by age sixty-five. These numbers are alarming, but in regions of the world closer to the equator, the rates of skin cancer are even higher.

In some regions of Australia for example, the probability of non-indigenous people (most of whom are of European descent) developing skin cancer at some point during their lifetime approaches 100%. Skin cancers are now the main cause of death in Australia of all persons between the ages of 25 and 40. Worldwide, skin cancer is expected to become the leading cause of death due to malignant disease in the next decade.

How did this alarming situation come about? The worldwide pandemic of skin cancers is probably not due to a single cause but more likely is due to a number of causal factors. These include lifestyle choices (suntanning, increased outdoor leisure activities), an aging population (accumulated skin damage due to chronic sun exposure and decreased DNA repair capacity with age) dietary factors (folic acid is the most common nutritional deficiency in the world and other micro-nutrient deficiencies) and environmental factors (workplace hazards and depletion of the ozone layer). In addition to increased risk of skin cancer, exposure to sunlight has a variety of adverse effects on the human body, including erythema (burning of the skin), photoaging (wrinkling) and suppression of the immune system. Recently, it has also been suggested that sunlight exposure in women might also increase the risk of neural tube defects in the developing fetus and risk of developing endometriosis (a condition characterized by invasion of the inner lining (endometrium) tissue into the outer layers of the uterus.)

Many of the effects of solar light on the human body are interrelated. For example, children who experience only a single episode of blistering sunburn in childhood (before the age of 18) double their risk of developing skin cancer later in life. Tanning of the skin was long thought to be an important component of a healthy lifestyle. It is now considered by most experts to be quite the opposite and should be more properly considered as the unhealthy appearance of sundamaged skin. In addition, contrary to another widely held belief, it is now well documented that tanning confers no protection whatsoever against the most serious effect of chronic sun exposure, the increased risk of skin cancer.

The skin cancers induced by sunlight can be broadly categorized into two types: melanomas and non-melanomas (basal cell and squamous). It was generally accepted for some time that exposure to UVB (the burning rays of the sun with the wavelengths ranging from 280 to 315 nm) was responsible for the induction of melanomas, the most serious form of skin cancer and the tumor type responsible for most deaths. This was held to be especially true in those individuals who had at least one episode of severe sunburn early in childhood. It seems likely from more recent studies, (especially an elegant series of experiments by Dr Richard Setlow reported recently to the annual meeting of the American Academy of Dermatology) that this is simply not the case. Based on spectral and mutational fingerprint analysis (each type of UV light causes a characteristic mutational pattern in target genes) Dr Setlow has suggested that melanomas are due mainly to chronic exposure to UVA. Wrongly considered by many people to be the harmless tanning rays of the sun, UVA has wavelengths between 320 and 400 nm. UVA has less energy than UVB but is more penetrating and passes through window glass and into deeper layers of the skin more easily.

There are several implications of this more detailed understanding of the carcinogenic potential of UVA and UVB. First, UVA light passes easily through the atmosphere and is not absorbed by the ozone layer. It is the main type of solar UV irradiation (about 95%) that reaches the surface of the earth. In the past, it was generally believed that UVA had only beneficial effects to humans such as stimulation of vitamin D formation and tanning. However, this is clearly not the case. Wavelengths in the UVA range are damaging to the skin, cause photoaging and are causally related to the induction of melanomas.

Second, depletion of the ozone layer and the concomitant increase in the amount of UVB light reaching the surface of the earth cannot be the explanation for the dramatic increase in melanomas seen worldwide in recent years. More likely it is due to the widespread use of sunscreen products that slow burning of the skin by filtering UVB and giving a false impression to the user that sun damage is not occurring. These individuals are not only at greater risk of melanoma formation but also increased risk of photoaging of the skin and suppression of their immune system.

Last, chronic exposure to UVA over the lifetime of an individual and not acute sunburn in childhood is now considered to be the main causative factor in the induction of melanomas, the most serious form of skin cancer and the type causing most deaths (six out of seven deaths due to skin cancer in the United States are caused by melanomas). The general implication of these findings is that tanning is unhealthy whether done in sunlight or by exposure to artificial sources of UVA such as those used in salons. The US FDA now recommends that people avoid tanning salons altogether and that sunscreen products should contain both UVA and UVB filters.

The mechanism of UV damage to skin is only partly understood. The harmful effects of UVA and UVB light on human skin are due primarily to direct cellular damage (see *Principles and Practice of Dermatology*, 2nd Edition, Williams and Wilkins, Churchill/Livingston, N.Y.). Suppression of the immune system also occurs but by an indirect mechanism. The genotoxic potential of solar light resides mainly in the ability of UV to damage DNA (DNA absorbs maximally at 254 nm). UV light causes the formation of various photoproducts in the strands of the DNA molecule. The major photoproducts caused by UV light are dimers (fusions) of adjacent pyrimidines (thymine or cytosine residues) in one of the two strands of the DNA molecule. Other minor products like 6,4 photoproducts also occur. DNA is not the only target of UV light. UV also damages other cellular components such as collagen and causes photoaging of the skin. But the main genotoxic (mutagenic and carcinogenic) effects of UV light seem to reside in the ability of UV wavelengths to damage DNA. The cancer causing effects of UV light are can also reside in the ability of these wavelengths to impair the body's immunosurveillance system whose job it is to detect and destroy potentially malignant cells. In the absence of a properly functioning immunosurveillance system, cells harboring tumorigenic mutations caused by sunlight are more likely to proceed to malignancy. In the art, numerous screening and filtering agents have been developed over many years, to protect skin against the deleterious affects of UV light. These agents are applied directly to the skin of a subject, and are believed to prevent UV light from penetrating the epidermis by acting as "filters," thereby absorbing or otherwise dissipating the energy contained in photons of UV light. Previously it was widely accepted in the industry that agents called "sunblocks" decreased UV-induced DNA damage, and in particular, pyrimidine dimer formation by UV opaque substances. In support of this view a recent clinical study indicated that "sunblocks" such as titanium oxide significantly reduced the incidence of pre-cancerous skin lesions in sunlight-exposed subjects.

However, the Food and Drug Agency (FDA) no longer accept the term "sunblock". The FDA believes the term is misleading as no agent truly "blocks" all harmful UV rays and the term should be disallowed as it implies a greater degree of protection from the damaging effects of sunlight than is warranted.

Para-aminobenzoic acid (pABA) was one of the first sunfiltering agents to be identified in the art. It is now seldom used because of problems with contact dermatitis. Due to widespread use of PABA over many years about 10% of all users of sunscreen products have some degree of contact sensitivity to the compound. However, esters of PABA, particularly octyl, dimethyl, para-aminobenzoic acid, do not elicit these same skin reactions. Other commonly used sunfilters are compounds from the salicyclate, cinnamate, benzophenone, anthranilate, and dibenzoylmethane families of molecules. It is well known in the art to combine sunfiltering agents that absorb UV light in different portions of the spectrum. However, most of these agents are synthetic chemicals not found in commonly in nature and it is not known what effects long-term use of these compounds may have on the human body.

Sunscreen compositions exert their effects through filtering or absorbing UV light so that the damaging wavelengths do not penetrate the various layers of the skin. To be effective, sunscreens must be present on the skin as a continuous film, and must remain on the surface of the skin throughout the period of UV exposure. One of the problems with products currently in use is that despite numerous attempts to develop topical compositions that act as sunscreen carriers and remain on the surface of the skin (see U.S. Pat. No. 5,087,445), sunscreens tend to rub off on towels and clothing, and wash off in perspiration, or during swimming, showering and bathing. Even if carriers are developed that remain on the surface of the skin for longer periods absorption of sunscreen (and cosmetic) additives into the skin remains a problem. This is due to the surprising fact that many sunfiltering agents used as sunscreen and cosmetic additives themselves cause DNA damage. Titanium dioxide for example a very common additive has long been considered to be safe and effective as a sunscreening agent. This may not be the case (see Salinaro et al., 1997, "Chemical oxidation and DNA damage catalyzed by inorganic sunscreen ingredients" FEBS Lett 418:87–90). Padimate-O, another common sunscreen additive in widespread use may also be genotoxic (see P. J. McHugh and J. Knowland, 1997, "Characterization of DNA damage inflicted by free radicals from a mutagenic sunscreen ingredient and its location using an in vitro genetic reversion assay" Photochem Photbiol 66:276–281.]

A recent research article (G. J. Cameron et al., 1997, "Systemic absorption of sunscreen after topical application" The Lancet 350: 863–864) has shown that the UVA sunscreen oxybenzone, a benzophenone derivative used commonly worldwide to make sunscreen products with high sun protection factors (SPF) is absorbed systemically and excreted in human urine soon after application to the skin. The repeated use of a sunscreen that is absorbed systemically could pose an especially high risk to human health if the sunscreen agent is chronically genotoxic. Taken as a whole, these data suggest that many of the sunscreen agents currently in widespread human use are carcinogenic. This has added a new urgency to the development of novel non-genotoxic sunfiltering agents. These agents should not only be effective in reducing the harmful effects of UV light, but also should be safe for human use, even upon repeated usage and over a long period of time. The present invention is submitted in an attempt to address this need.

BRIEF DESCRIPTION OF THE DRAWINGS

Preferred embodiments of the invention will be described below in relation to the figures in which.

SUMMARY OF THE INVENTION

Figure 1:
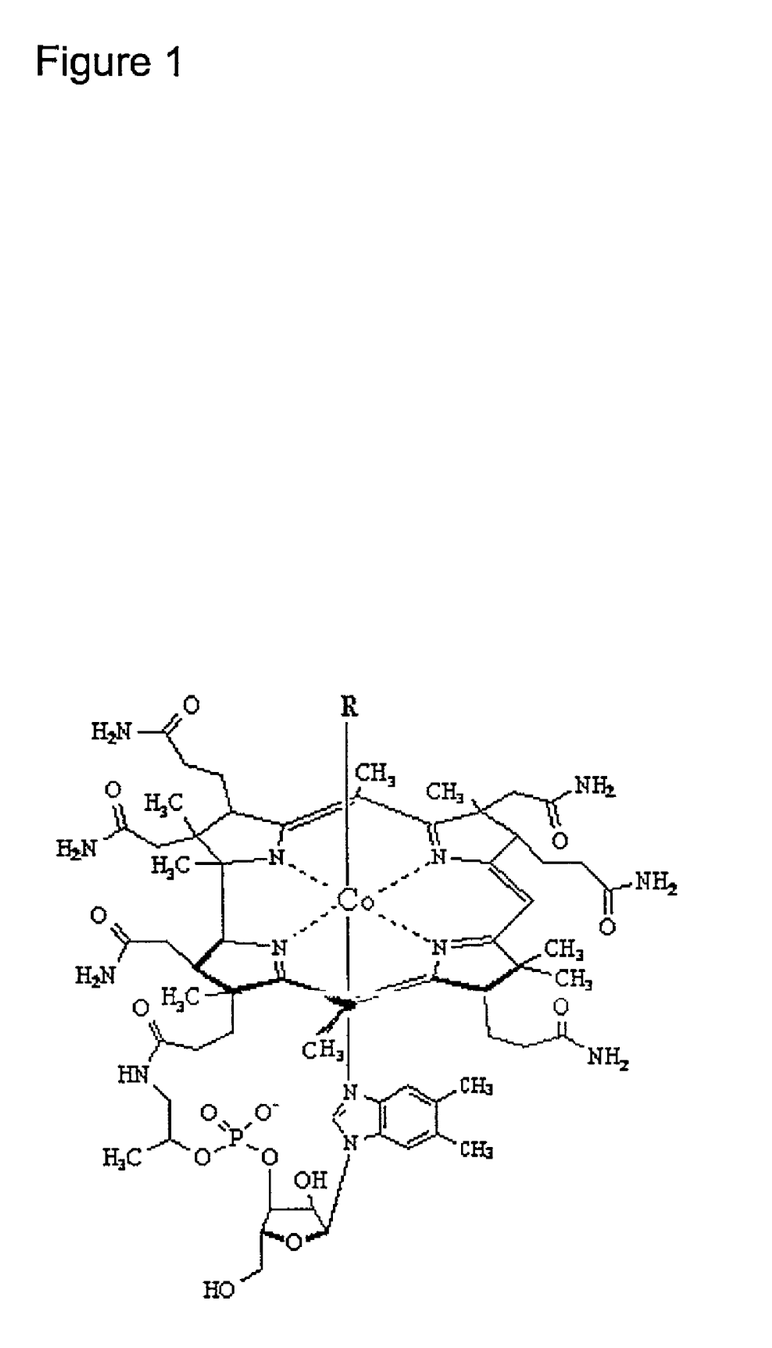
FIG. 1 is the chemical structure of vitamin B12 wherein R is defined as OH, CN, $NO_2$, $CH_3$, or 5'-deoxy-adenosyl.
Figure 2:
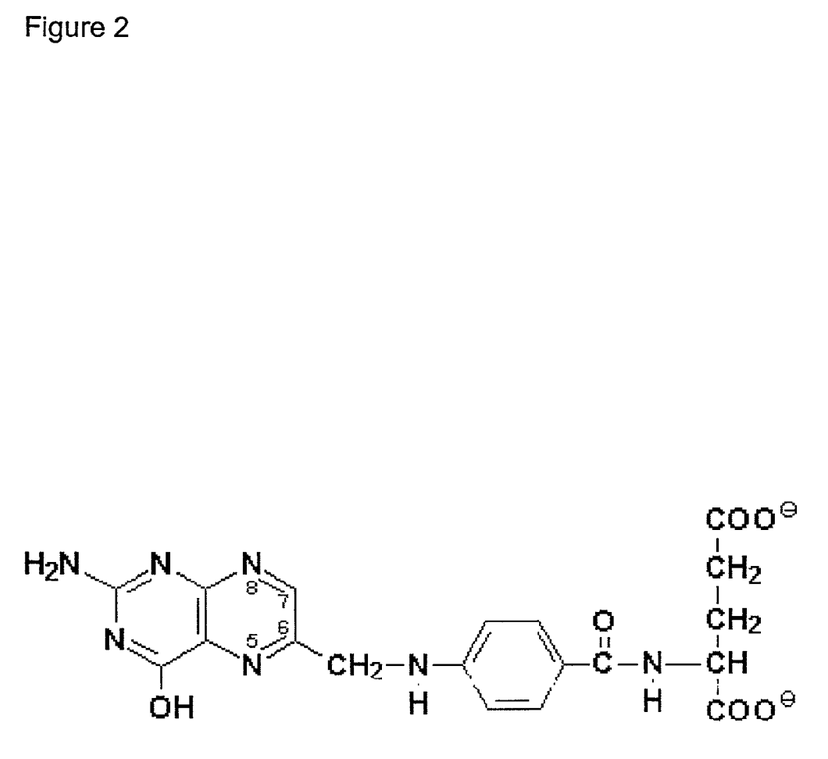
FIG. 2 is the chemical structure of folate (vitamin B9).
Figure 3:
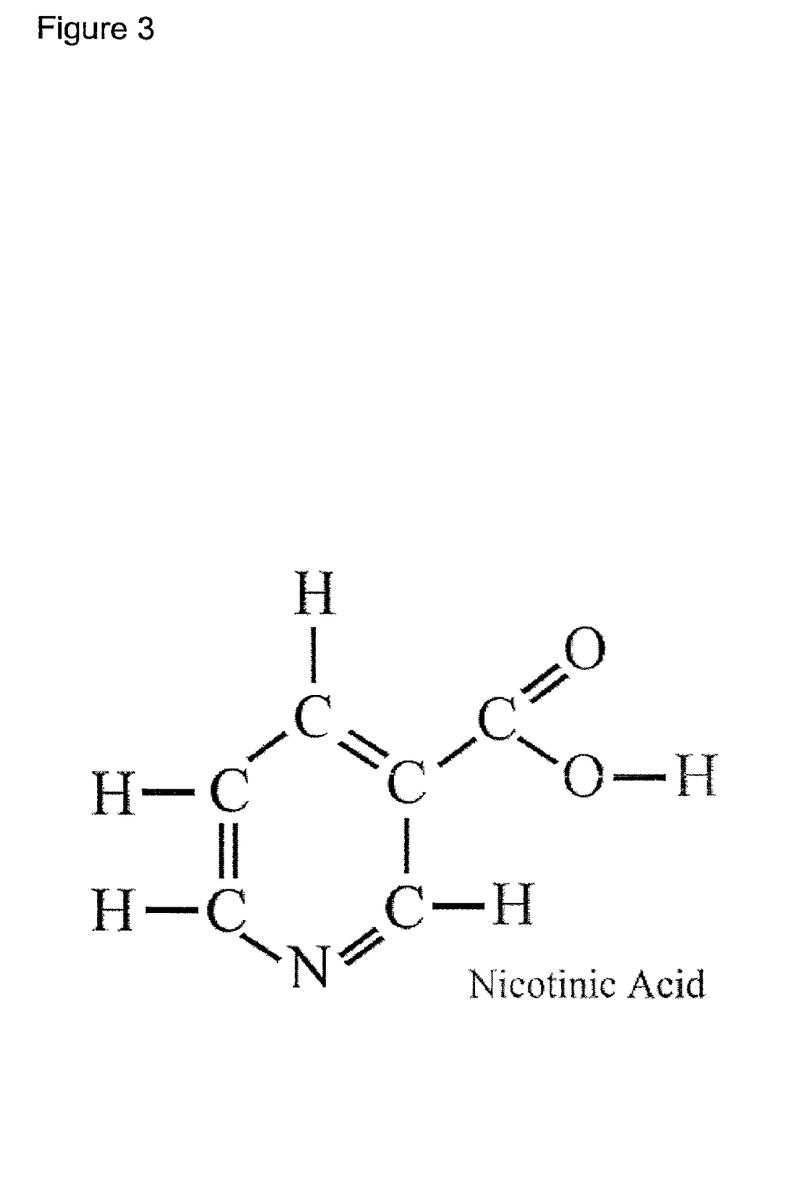
FIG. 3 is the chemical structure of niacinamide (vitamin B3).

The object of the invention is to provide a means of reducing the burning, genotoxic, immunosuppressive and photoaging effects of UV light by application of three common B vitamins to the skin The terms "vitamin B12 derivative", "folate derivative" (vitamin B9 derivative) and "niacinamide derivative" (vitamin B3), include the precursors (pro-vitamins), metabolites, derivatives, and conjugates of the parent compounds, all of which may be either naturally occurring or synthetic, as well as the salts of the compounds. Folate derivatives include polyglutamated derivatives. Results of experiments with human volunteers described below have shown that the combination folic acid, vitamin B12 and niacinamide when taken in pill form prevented sunburning for many hours. Topical application would be effective in a similar fashion. Broadly speaking, the invention provides a method for reducing or inhibiting a disease or disorder in a mammal caused by ultraviolet radiation comprising exposing the cells to an amount of at least one of vitamin B12 or B9 but preferably the two vitamins in combination with niacinamide, in appropriate concentration, which is sufficient to reduce UV damage to cells, specifically skin cells.

In a preferred embodiment, the invention is a method for reducing or inhibiting a disease or disorder in a mammal caused by UV radiation comprising administering to the subject a formulation of vitamin B12, vitamin B9 and vitamin B3, in a suitable carrier, the amounts of each individual component sufficient to reduce UV damage to cells. The carriers are compatible (cosmetically or otherwise) with the route of administration. The carriers for oral, parenteral, enteral, entranasal, rectal or ocular administration are preferably at least one of water, gas, a water-based liquid, an oil, a gel, an emulsion, a dispersion or a mixture thereof.

The carriers for topical administration are preferably at least one of a lipid, water, gas, a water-based liquid, oil, a gel, an emulsion, dispersion or a mixture thereof. In an alternate embodiment, the carrier is an ester, preferably an ester of para-aminobenzate, such as, ocytl- and dimethyl-para-aminobenzoic acid.

The vitamin B9 is preferably at least one of either folic acid, dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid and 5-methyltetrahydrofolic acid or derivatives thereof.

In a particularly preferred embodiment, the folate is leucovorin, folic acid, or a combination of these two folates.

In one preferred embodiment, folate is present in the composition at a concentration in the range of approximately 0.2 mg/ml to 10 mg/ml and, the carrier is suitable for topical application. Niacinamide is present at 2.0 mg/ml to 100 mg/ml. Vitamin B12 is present in the range 0.1 mg/ml to 1 mg/ml.

In another preferred embodiment, a folate is present in the composition in an amount of about 200 ug to about 10 mg by dry weight, niacinamide in an amount of about 20 mg to about 1 g by dry weight, vitamin B12 is present in an amount of about 20 ug to about 1.5 mg by dry weight and the carrier is suitable for oral administration to children. In another preferred embodiment, a folate is present in the composition in an amount of about 1 mg to 10 mg by dry weight, nicacinamide in an amount of about 100 mg to about 1 g by dry weight, vitamin B12 is present in an amount of about 0.1 mg to about 1.5 mg by dry weight and the carrier is suitable for administration to adults. In a particularly preferred embodiment, the folate is leucovorin, folic acid, or a combination of these two folates or their pharmaceutically acceptable salts.

In a variation, the invention is a method for reducing or inhibiting a disease or disorder in a mammal caused by UV wherein the pharmaceutical composition for use as a sunscreen further includes at least one cosmetically acceptable adjuvant or additive, such as preservative, organic solvent, browning agent, antioxidant, stabilizer, emollient, silicone, alpha-hydroxy acid, demulcent, anti-foaming agent, moisturizing agent, vitamin, fragrance, ionic or nonionic thickener, surfactant, filler, thickener, sequestrant, polymer, propellant, alkalinizing or acidifying agent, opacifier, fatty compound or colorant.

In another embodiment, the invention is a method for reducing or inhibiting a disease or disorder in a mammal caused by UV wherein the pharmaceutical composition for use as a sunscreen further includes at least one sunfiltering or sunscreening compound such as para-aminobenzoic acid, salicyclate, cinnamate, benzophenone, anthranilate, dibenzoylmethane, beta-carotene and alpha-hydroxy acids.

The pharmaceutical compositions for use as a sunscreen for protecting the human skin, human hair or another surface from ultraviolet radiation include vitamin B12, niacinamide, at least one folate, and a suitable carrier. The carriers are compatible (cosmetically or otherwise) with the route of administration. The carriers for oral, parenteral, enteral, entranasal, rectal or ocular administration are preferably at least one of water, gas, a water-based liquid, an oil, a gel, an emulsion, a dispersion or a mixture thereof.

The carriers for topical administration are preferably at least one of a lipid, water, gas, a water-based liquid, oil, a gel, an emulsion, dispersion or a mixture thereof. In an alternate embodiment, the carrier is an ester, preferably an ester of para-aminobenzate, such as, ocytl- and dimethyl-para-aminobenzoic acid.

The pharmaceutical compositions protect skin, hair and eyes from solar radiation. Suitable compositions include an oil-in-water emulsion or a water-in-oil emulsion. In a variation, the pharmaceutical composition for use as a sunscreen further includes at least one cosmetically acceptable adjuvant or additive, such as preservative, organic solvent, browning agent, antioxidant, stabilizer, emollient, silicone, alpha-hydroxy acid, demulcent, anti-foaming agent, moisturizing agent, vitamin, fragrance, ionic or nonionic thickener, surfactant, filler, thickener, sequestrant, polymer, propellant, alkalinizing or acidifying agent, opacifier, fatty compound or colorant.

In another embodiment, the pharmaceutical composition further includes at least one sunfiltering or sunscreening compound such as para-aminobenzoic acid, salicyclate, cinnamate, benzophenone, anthranilate, dibenzoylmethane, beta-carotene and alpha-hydroxy acids.

Other useful compositions are a nonionic vesicle dispersion, emulsion, cream, milk, gel, ointment, suspension, dispersion, powder, solid stick, foam or spray. The composition may also include a hair rinse, spray, mist, gel, mousse, shampoo, conditioner, lotion, emulsion and coloring product.

The claimed invention has the advantage that administration of the vitamin mixture containing vitamin B12, such as, cobalamin, cyanocobalamin, methylcobalamin and adenosylcobalamin., a folate, and niacinamide, for the purposes of reducing UV damage to the cells of a subject can be done either topically, systemically (orally or by injection), or via a combination of routes. Systemic delivery of the vitamin mixture might afford protection to the eye, something that cannot readily be accomplished by commercially available topical sunscreens. Such a treatment might be expected to lessen the risk of cataracts induced by UV light. Secondly, protection from UV light by a naturally occurring compound may avoid exposure to chemicals that may be toxic, genotoxic (mutagenic or carcinogenic) or irritating to the subject. Thirdly, the invention provides a method to filter or absorb harmful UV rays through the use of bioavailable compounds. Bioavailable compounds are chemicals, usually from natural sources, that are readily taken up and metabolized by cells. Because these compounds are simple B complex vitamins with other known effects their ingestion or topical application may have other health benefits than those described herein. For example subjects who have taken the three vitamin formulation described herein have reported an amelioration of symptoms of a variety of dermatological conditions including acne vulgaris, actinic keratoses, photodermatitis and certain types of psoriasis "sun allergy" including discoid lupus erythematosus. This suggests the possibility of a specific treatment for photosensitivity to UV light by the invention caused by a variety of medical conditions including but not limited to xeroderma pigmentosum, albinism, or treatment by a number of drugs. The claimed invention may be used for the prevention and treatment of disorders of the skin, the immune system, disorders of the hematopoietic system and cancer. The invention may also be used for protecting plant cells from solar UV. The invention may be sprayed onto plants. Other features and advantages of the invention will be evident from the following description and the claims.

DETAILED DESCRIPTION OF THE INVENTION

Folates

A number of folates, described below, are applicable to the invention. "Reduced folates," means folates at the dihydro and tetrahydro level of oxidation, for example folinic acid or folinate. The folates referred to above include, but are not limited to, the following: folic acid, dihydrofolic acid, tetrahydrofolic acid, 5-formyltetrahydrofolic acid (folinic acid, leucovorin), 10-formyltetrahydrofolic acid, 5-10 methylenetetrahydrofolic acid, 5-10 methenyltetrahydrofolic acid and 5-methyltetrahydrofolic acid. Of these, folic acid and folinic acid and their salts are preferred.

Folic acid is formed from three separate chemical building blocks:

A heterocyclic pteridine ring, 6-methylpterin
p-aminobenzoic acid (pABA), and
glutamic acid.

The 6-methylpterin moiety is linked through the amino group on pABA to form pteric acid, which is in turn linked through an amide to glutamate. Pteric acid that is linked to a single glutamate is known as pteroylmonoglutamate. However, many naturally occurring folates have additional glutamate residues attached to pteric acid (pterylpolyglutamates). The additional glutamate residues, linked by means of a modified peptide bond involving the alpha-amino group of one glutamate and the gamma-carboxyl group of another, allow for compartmentalization of different reduced folates in cells and provide an additional level of regulation for folate interconversion enzymes.

It is believed that only the monoglutamate forms of folate are transported into human cells. Other glutamate groups are added subsequently. One function of these polyglutamated derivatives is to maintain intracellular pools of reduced folates. The term folate, as used herein includes such polyglutamated derivatives.

Humans cannot synthesize folic acid de novo. Inside cells, folic acid is metabolized to dihydrofolate and then to tetrahydrofolate by means of an enzyme known as dihydrofolate reductase (DHFR). Tetrahydrofolate is converted to a variety of reduced intermediates involved in the mobilization and utilization of single-carbon functional groups (i.e. methyl, methenyl, methylene and formyl). These one-carbon donors function in the metabolism of certain amino acids such as serine, glycine, methionine, and histidine, and in the biosynthesis of purine and pyrimidine nucleotides. In the latter pathway a reduced folate donates the methyl group of thymine via thymidylate synthase without which cells lack one of the basic building blocks of DNA synthesis. Consequently, depletion of reduced folates (usually due to DHFR inhibition) is lethal to cells. The effects of partial folate starvation on cells is not known but it is reasonable to suppose that they are impaired in nucleotide synthesis and thus cannot synthesize and repair DNA at normal rates.

Many folates exist in nature, but they can also be manufactured by chemical synthesis. For purposes of this application, the term folate encompasses both naturally occurring and synthetic forms.

Folates can be used as a single chemical species or a mixture of two or more species. It is anticipated that a mixture of folates may be more effective than a single species. For example, the UV absorption spectra of folic acid and folinic acid cover a broader spectrum of absorption than either compound alone.

Some of the folates of the invention can be obtained commercially from a number of sources. Folic acid, folinic acid and 5-methyltetrahydrofolate acids are available from Sigma Chemical Co., St Louis Mo. Other folates that are not commercially available can be prepared by a chemist of ordinary skill in the art, (see U.S. Pat. No. 5,410,056, which is incorporated by reference in its entirety).

Conjugates of the folates such as those with amino acid side chains can be prepared by published methods (see Ayling, J. and Baugh, N., *Chemistry and Biology of Pteridines and Folates*, 1993, Plenum Press N.Y., which is hereby incorporated by reference in its entirety).

The folates of the invention need not be highly purified. Mixtures of partially purified folates can be used. Folates or combinations of folates can be tested for their ability to protect cells from UV light, by using the a screen such as the human fibroblast cell culture system described herein. The folates to be tested would be added to cultures of mammalian cells before, during or after exposure to UV light. Folates that are effective blocks to UV light would increase cell survival.

Vitamin B12 and Niacinamide

A detailed description of these vitamins including dietary reference intake recommendations and lack of side effects for these vitamins can be found in "Dietary Reference Intakes for Thiamin, Riboflavin, Niacin, Vitamin B6, Folate, Vitamin B12, Pantothenic Acid, Biotin and Choline" A Report on the Scientific Evaluation of Dietary Reference Intakes and its Panel on Folate, Other B Vitamins, and Choline and Subcommittee on Upper Reference Levels of Nutrients. Food and Nutrition Board Institute of Medicine. National Academy Press, Washington D.C. 1998. The above document is included in the present application by reference in its entirety.

Administration of the B Vitamin Formulation

The methods of the invention are applicable to cells of any organism that can potentially be damaged by UV light. For the purposes of this patent application, the term "subject" means a whole multi-cellular organism, which includes humans, lower animals and plants. In a preferred embodiment, the methods and compositions are applied to human cells, particularly human cells which are subject to sun exposure, such as melanocytes, and the squamous and basal cells of the dermis and epidermis.

For cells that are maintained in tissue culture, the vitamins are administered by adding them to the growth medium in which the cells are maintained.

For whole organisms, including humans, the compounds may be administered topically, by applying them to the outside skin or surface of the organism. Without being bound by any theory, it is suggested that the B complex vitamins used in the invention act both inside and outside the treated cells. Many types of cells are permeable to at least some of the vitamins that are used to carry out the invention. For example, mouse L1210 cells, can take up folates such as 5-methyltetrahydrofolate, by at least two mechanisms; a specific transporter in the cell membrane that operates in the micromolar range and a second transport system that takes up folates in the nanomolar range.

A lack of permeability to a particular vitamin does not necessarily exclude the compound from intracellular use. Various methods can be used to facilitate the entry of the folates into cells. For example, the liposome-mediated methods, which have been developed for the delivery of DNA repair enzymes (i.e. T4 endonuclease or photolyase), as mentioned above, can be adapted to deliver the three B complex vitamins into cells. Such methods are disclosed in U.S. Pat. Nos. 5,077,211 and 5,352,458, which are hereby incorporated by reference in their entirety. For purposes of administration of the three B vitamins alone or in combination to a subject, they are incorporated into a pharmaceutically acceptable carrier, which can take many different forms. By "pharmaceutically-acceptable" is meant that the carrier comprises common pharmaceutical and cosmetic ingredients that are generally recognized as safe for human use.

Useful pharmaceutical carriers for the preparation of the pharmaceutical compositions hereof can be solids, liquids or gases. Water, saline, aqueous dextrose and glycols are preferred liquid carriers, particularly for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glyerol, monosterate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, Remington's Pharmaceutical Sciences, 15$^{th}$ Ed. (Mack Publishing Co., Easton 1975) (see, e.g., pp.1405–1412, 1461–1487). Such compositions will, in general, contain an effective amount of the active compound together with a suitable amount of carrier so as to prepare the proper dosage form for proper administration in the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

A suitable topical carrier can be in the form of a water-in-oil emulsion; these emulsions can be thin or thick in consistency, so as to be adaptable to spray or aerosol delivery, lotions, creams, etc. Other useful carriers for topical administration include any of gases, water, water-based liquids, lotions, dispersions, oils, oil-based solutions, powder, gels, emulsions, dispersions or mixtures thereof. Some folates are water-soluble, and can be used without an oil component in the carrier. The appropriate amount of carrier can readily be determine by those skilled in the art according to the SPF desired. Hydrophobic carriers as well as hydrophilic carriers may be employed with the sunscreen compositions. Carriers to be applied to the skin or hair are compatible with human skin or hair, respectively. Ansel et al. describe many appropriate carriers for topical administration in the above-noted reference. Other appropriate carriers are disclosed in the following patents, hereby incorporated by reference: U.S. Pat. Nos. 4,401,664, 4,938,969, 5,607,622, and 5,153,230.

Additional sunscreen agents known in the art may also be added to the compositions, for example, at least one additional hydrophilic or lipophilic organic UV-A and/or UV-B sunscreen agent such as cinnamate, benzophenone, beta-carotene, and alpha-hydroxy acids. In particular, Vitamin E (alpha-tocopherol), often used in commercial skin care products could be incorporated into the composition.

The compositions of the invention may also include, in addition, conventional cosmetic adjuvants and additives such as preservatives, organic solvents, browning agents, antioxidants, stabilizers, emollients, silicones, alpha-hydroxy acids, demulcents, anti-foaming agents, moisturizing agents, vitamins, fragrances, ionic or nonionic thickeners, surfactants, fillers, thickeners, sequestrants, polymers, propellants, alkalinizing or acidifying agents, opacifiers, fatty compounds (e.g. oil, wax, alcohols, esters, fatty acids), colorants, or mixtures thereof or any other ingredient that may be used in cosmetics and in particular for the production of sunscreen compositions.

The invention also relates to a method of protecting human skin or hair against the deleterious effects of solar radiation by topically applying thereto an effective amount of a composition of the invention.

Compositions for hair or other personal care may be prepared by adding UV screening compounds in hair rinses, aerosol sprays, mists, gels, mousses, shampoos, conditioners, lotions, films, emulsions and coloring products to reduce photodamage to hair and photobleaching of hair and hair dyes. The invention also relates to a method of protecting human hair against the deleterious effects of solar radiation by topically applying thereto an effective amount of a composition of the invention.

Makeup products such as foundation, lipstick, eyeshadow, blush, nail polish, mascara, moisturizing creams and lotions or eyeliner may also contain the compounds of the invention. These are formulated according to known methods for makeup products such as those for preparation of an anhydrous or aqueous solid or paste, emulsion, suspension or dispersion.

The composition may also contain agents that promote absorption into the skin, for example, propylene glycol, which was used in Example 1 and 2. The folate compounds of the invention could also be administered in liposomes, or liposomes that also contain DNA repair enzymes such as AP endonuclease If it is desired to deliver the three B vitamins into cells, oral, enteral, entranasal, rectal, ocular or parenteral routes can be used. Methods and compositions for administration via oral enteral, entranasal, rectal, ocular and parenteral routes are well known in the art. (For example, see Ansel, A. C., Popovich, N. G., and Allen Jr., L. V. *Pharmaceutical Dosage Forms and Drug Delivery Systems*, 6th Edition. 1995. Williams & Wilkings, Baltimore, which is hereby incorporated by reference in its entirety.)

Topical application to the epidermis of a subject can also be an effective route to deliver bioavailable folates, niacinamide and vitamin B12, including cobalamin, cyanocobalamin, methylcobalamin and adenosylcobalamin.

The B complex vitamin formulation could also be administered via micro sponge delivery system, as described in K.

Embil and S. Nacht, 1996, "The micro sponge Delivery System (MDS): a topical delivery system with reduced irritancy incorporating multiple triggering mechanisms for the release of actives" J Microencapsul 13: 575–588.

Although topical or oral delivery would seem the most practical, for some human subjects who are extremely light sensitive due to treatment with various prescription medicines (e.g. tetracycline) or who are afflicted with certain medical conditions (e.g. burn patients) or genetic disorders (e.g. xeroderma pigmentosum), it is conceivably advantageous to deliver the composition systemically by means of intravenous, subcutaneous or intramuscular routes.

The appropriate concentration of folates in the composition to be administered to a subject varies depending on the particular folate, the route of administration, and the cells to which it is targeted. However, for intracellular effects, the concentration of folates should be tailored to result in the accumulation in the cells of sufficient concentrations of the three B complex vitamins to reduce UVR damage to the cells. For UV absorption or blocking on the outer surfaces of the subject, the concentration of vitamins should be adjusted to result in the desired degree of absorption or blocking.

The particular dosage of pharmaceutical composition to be administered to the subject topically will depend on a variety of considerations including the schedule of administration, the age and physical characteristics of the subject, and so forth. Proper dosages may be established using clinical approaches familiar to the medicinal arts. Preferably, the concentration of folates in the composition is between (0.002 and 10 mg/ml), and more preferably between (0.002 mg/ml and the limits of solubility of the folate compound in any particular carrier). The concentration of niacinamide will be 100 times this amount. The vitamin B12 concentration will be in the range 0.1 mg/ml to the limits of solubility of the vitamin. The topical composition can be reapplied periodically during sun exposure to replace removed or absorbed material.

If the three B complex vitamins are administered orally, the composition, in a suitable carrier can be administered in single unit dosage form with continuous therapy or in single dose therapy ad libitum. The composition could be administered in the form of tablets, pills, capsules, powders, enterically coated or other protected formulations (such as binding on ion exchange resins or other carriers, or packaging in lipid protein vesicles or adding additional terminal amino acids), sustained release formulations, solutions (e.g., ophthalmic drops), suspensions, elixirs, aerosols, and the like. The compositions could also be administered orally or sublingually or in the form of a juice or other suitable drink or other suitable dietetic composition.

The particular dosage of pharmaceutical composition to be administered to the subject orally, parenterally, enterally, entranasally, rectally or ocularly will depend on a variety of considerations including the schedule of administration, the age and physical characteristics of the subject, and so forth. The pharmaceutical compositions to be administered orally, parenterally, enterally, entranasally, rectally or ocularly to an adult should be in the range of about 0.1 mg to about 1.5 mg of vitamin B12, about 100 mg to about 1 g of vitamin B3 and about 1 mg to about 10 mg of vitamin B9. The pharmaceutical compositions to be administered orally, parenterally, enterally, entranasally, rectally or ocularly to a child should be in the range of about 20 ug to about 1.5 mg of vitamin B12, about 20 mg to about 1 g of vitamin B3 and about 200 ug to about 10 mg of vitamin B9. Proper dosages may be established using clinical approaches familiar to the medicinal arts. A daily dosage of folates in the range of 0.02 mg/kg to 0.05 mg/kg, and preferably between 0.02 mg/kg and 0.2 mg/kg, and more preferably between 0.02 mg/kg and 1 mg/kg can be ingested orally. The amount of niacinamide will be 100 times this amount. Vitamin B12 can be ingested in the range 0.001 mg/kg to 1 mg/kg.

A person skilled in the art can readily determine the effective amount of a particular B complex vitamin by a variety of common assay systems.

The pharmaceutical compositions are used to treat diseases caused by ultraviolet radiation, such as diseases or conditions of the skin and immune system. The pharmaceutical compositions are used to treat actinic keratoses, photodermatitis, photo-induced (discoid) lupus erthermatosus.

Experimental Evidence:

1. Over the period of four weeks a white middle aged couple in their forties on holiday in Mexico self administered 400–600 mcg vitamin B12/day in the form of 100 mcg tablets. Both reported a significant reduction in the rate of sunburning when exposed continuously to sunlight than (a) expectation and past experience when holidaying in Mexico and (b) when not taking the vitamin B12 daily supplement.

2. Over the period of a year and a half a white middle aged male self-administered vitamin B12 alone at 300 mcg to 500 mcg/day in the form of 100 mcg tablets, folic acid alone in the form of folic acid alone at 2 mg–5 mg/day in the form of 1 mg tablets or a combination of both vitamins in the same dose range taken with niacinamide 200 mg–500 mg/day in the form of 100 mg tablets. In all cases there was some amelioration of the expected sunburning effects of continuous sun exposure. Normal burning rates returned within 24 hrs of the cessation of oral administration of the various formulations.

3. The most effective formulation was the combination 500 mcg vitamin B12, 5 mg folic acid and 500 mg niacinamide which prevented sunburning over a period of 5½ hours. The published UVB index gave an expected time of continuous exposure to sunlight in the Edmonton AB area of 45 minutes. The maximum SPF (skin protection factor) was computed to be approximately 330/45=7.3.

4. The most effective method of administration was the dose of the three vitamins given in (3) taken orally the night before and again the morning of the same day as sun exposure.

5. These experiments have been repeated with approximately twenty human volunteers of various skin types ranging in age from 25 to 35 years. Most were female, one was a qualified physician, and many were qualified nurses or other healthcare professionals trained in observing symptoms of skin burning. Over the past year, a variety of different combinations of the three B complex vitamins were tested by exposure of these individuals to direct sunlight in locales such as Alberta Canada, Kelowna Canada, Mexico, Montego Bay Jamaica, San Diego Calif., Phoenix Ariz., Los Angeles Calif., and Honolulu, Hi. either in the course of their work or on vacation. The subjects had various skin types and were of many different nationalities.

6. In all cases the subjects in (5) reported an ameliorating effect of the methods and compositions for the B complex vitamin formulation described in the present application.

7. We identify the role of folate in the repair of UVB damage in folate deficient yeast cells, human fibroblasts and in mice. Moreover we show yeast cells harboring multiple copies of the gene encoding dihydrofolate reductase are resistant to the killing effects of UV light. The experiments show an absolute requirement for folate in the normal repair of UV damaged DNA and by inference in the etiology of human skin cancers.

8. We identify plants resistant to UV radiation damage with a method comprising providing a set of plants and selecting from the set plants, which have high levels of reduced folates.

The present invention has been described in detail and with particular reference to the preferred embodiments; however, it will be understood by one having ordinary skill in the art that changes can be made thereto without departing from the spirit and scope thereof. For example, where polypeptides are described, it will be clear that peptides and proteins can often be used.

All publications, patents and patent applications are incorporated by reference in their entirety to the same extent as if each individual publication, patent or patent application was specifically and individually indicated to be incorporated by reference in its entirety.

The embodiments of the invention in which an exclusive property or privilege is claimed are defined as follows:

1. A method for treating or preventing damage to skin cells in a mammal caused by ultraviolet radiation, comprising administering an effective amount of a vitamin selected from the group consisting of B12 having the formula:

wherein R is OH, CN, NO$_2$, CH$_3$, or 5'-deoxy-adenosyl, derivatives thereof, vitamin B3, derivatives thereof, vitamin B9, derivatives thereof, and mixtures thereof.

2. The method of claim 1, wherein the vitamin B12 is administered topically, orally, parenterally, enterally, entranasally, rectally or ocularly.

3. The method of claim 1 or 2, wherein the vitamin B12 is administered before, during or after the mammal is exposed to ultraviolet radiation.

4. The method of claim 1, wherein the vitamin B12 is administered in a sunscreen composition comprising vitamin B12 and a carrier or excipient.

5. The method of claim 4, wherein the carrier is a member selected from the group consisting of lipids, esters, solid inert diluents, liquid inert diluents, water, a gas, a water-based liquid, an oil, a gel, an emulsion, a dispersion, and mixtures thereof.

6. The method of claim 5, wherein the ester comprises an ester of para-aminobenzoate selected from the group consisting of ocytl- and dimethyl-para-aminobenzoic acid.

7. The method of claim 4, wherein the composition further comprises at least one compound selected from the group consisting of para-aminobenzoic acid, salicyclate, cinnamate, benzophenone, anthranilate, dibenzoylmethane, beta-carotene, alpha-hydroxy acids, titanium dioxide and padimate-o.

8. The method of claim 4, wherein the composition further comprises at least one cosmetically acceptable adjuvant or additive selected from the group consisting of a preservative, organic solvent, browning agent, antioxidant, stabilizer, emollient, silicone, alpha-hydroxy acid, demulcent, antifoaming agent, moisturizing agent, vitamin, fragrance, ionic or nonionic thickener, surfactant, filler, thickener, sequestrant, polymer, propellant, alkalinizing or acidifying agent, opacifier, fatty compound and a colorant.

9. The method of claim 4, wherein the composition comprises vitamin B3 or a derivative thereof.

10. The method of claim 9, wherein the vitamin B3 is niacinamide.

11. The method of claim 4, wherein the composition comprises vitamin B9 or a derivative thereof.

12. The method of claim 11, wherein the vitamin B9 is selected from the group consisting of folic acid, dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid, and 5-methyltetrahydrofolic acid or derivatives thereof.

13. The method of claim 4, wherein the composition comprises vitamin B3 or a derivative thereof, and vitamin B9 or a derivative thereof.

14. The method of claim 13, wherein the vitamin B3 is niacinamide and the vitamin B9 is selected from the group comprising folic acid, dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid, 5-10 methylenetetrahydrofolic acid or derivatives thereof.

15. The method of claim 4, wherein the vitamin B12 is present in an amount of about 0.1 mg/ml to 1 mg/ml.

16. The method of claim 9, wherein the vitamin B3 is present in an amount of about 2 mg/ml to about 100 mg/ml.

17. The method of claim 11, wherein the vitamin B9 is present in an amount of about 0.2 mg/ml to about 10 mg/ml.

18. The method of claim 2, wherein the vitamin B12 is administered as a pharmaceutical composition comprising vitamin B12 and a pharmaceutically acceptable carrier or excipient.

19. The method of claim 18, wherein the carrier comprises water, gas, a water-based liquid, an oil, a gel, an emulsion, a dispersion or a mixture thereof.

20. The method of claim 18, wherein the carrier comprise a lipid.

21. The method of claim 18, wherein the composition further comprises at least one DNA repair enzyme selected from the group consisting of T4 endonuclease or photolyase.

22. The method of claim 18, wherein the composition is administered as a formulation selected from the group consisting of tablets, dragees, suppositories, capsules, granules, solution, suspensions, and lyophilized compositions.

23. The method of claim 18, wherein the composition further comprises an additive selected from the group consisting of aggregants, disaggregants, osmotic pressure regulating salts, buffers, sweeteners, and coloring agents.

24. The method of claim 18, wherein the composition further comprises a fat-soluble antioxidant selected from the group consisting of ascorbyl palmitate, tocopherols and ascorbic acid in the presence of lecthin.

25. The method of claim 18, wherein the composition is administered as a formulation selected from the group consisting of tablets, dragees, capsules, suppositories, granules, solution, suspension, and lyophilized compositions.

26. The method of claim 18, wherein the composition further comprises vitamin B3 or a derivative thereof.

27. The method of claim 26, wherein the vitamin B3 is niacinamide.

28. The method of claim 18, wherein the composition further comprises vitamin B9 or a derivative thereof.

29. The method of claim 18, wherein the vitamin B9 is selected from the group comprising folic acid, dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid and 5-methyltetrahydrofolic acid or derivatives thereof.

30. The method of claim 18, wherein the composition further comprises vitamin B3 or a derivative thereof, and vitamin B9 or a derivative thereof.

31. The method of claim 30, wherein the vitamin B3 is niacinamide and the vitamin B9 is selected from the group comprising folic acid, dihydrofolic acid, tetrahydrofolic acid, 5-formyltetrahydrofolic acid, 10-formyltetrahydrofolic acid, 5-10 methylenetetrahydrofolic acid, 5-10 methenyltetrahydrofolic acid and 5-methyltetrahydrofolic acid or derivatives thereof.

32. The method of claim 18, wherein the amount of vitamin B12 to be administered to an adult is present in an amount of about 0.1 mg to about 1.5 mg.

33. The method of claim 26, wherein the amount of vitamin B3 to be administered to an adult is present in an amount of about 100 mg to about 1 g.

34. The method of claim 28, wherein the vitamin B9 to be administered to an adult is present in an amount of about 1 mg to about 10 mg.

35. The method of claim 18, wherein the amount of vitamin B12 to be administered to a child is present in an amount of about 20 ug to about 1.5 mg.

36. The method of claim 26, wherein the amount of vitamin B3 to be administered to a child is present in an amount of about 20 mg to about 1 g.

37. The method of claim 28, wherein the vitamin B9 to be administered to a child is present in an amount of about 200 ug to about 10 mg.

* * * * *